US00PP25699P3

(12) United States Plant Patent
Stewart et al.

(10) Patent No.: US PP25,699 P3
(45) Date of Patent: Jul. 14, 2015

(54) STRAWBERRY PLANT NAMED 'DRISSTRAWFORTYONE'

(50) Latin Name: *Fragaria ×ananassa*
Varietal Denomination: DrisStrawFortyOne

(71) Applicant: DRISCOLL STRAWBERRY ASSOCIATES, INC., Watsonville, CA (US)

(72) Inventors: Philip J. Stewart, Watsonville, CA (US); Renae Robertson, Santa Maria, CA (US); Joanne F. Coss, Pebble Beach, CA (US); Martin P. Madesko, Aptos, CA (US); Agustin M. Renteria, Royal Oaks, CA (US); Bruce D. Mowrey, Watsonville, CA (US)

(73) Assignee: DRISCOLL STRAWBERRY ASSOCIATES, INC., Watsonville, CA (US)

( * ) Notice: Subject to any disclaimer, the term of this patent is extended or adjusted under 35 U.S.C. 154(b) by 133 days.

(21) Appl. No.: 13/998,120

(22) Filed: Oct. 2, 2013

(65) Prior Publication Data

US 2015/0096087 P1 Apr. 2, 2015

(51) Int. Cl.
*A01H 5/08* (2006.01)

(52) U.S. Cl.
USPC ..... Plt./209

(58) Field of Classification Search
USPC ..... Plt./209, 208
See application file for complete search history.

*Primary Examiner* — Susan McCormick Ewoldt
(74) *Attorney, Agent, or Firm* — Jondle & Associates, P.C.

(57) ABSTRACT

A new and distinct variety of strawberry plant named 'DrisStrawFortyOne' particularly characterized by a dense plant bearing dark red fruit having a mid-season harvest maturity is disclosed.

3 Drawing Sheets

Genus and species: *Fragaria×ananassa.*
Variety denomination: 'DrisStrawFortyOne'.

BACKGROUND OF THE NEW PLANT

The present invention relates to a new and distinct strawberry variety designated 'DrisStrawFortyOne' and botanically known as *Fragaria×ananassa*. This new strawberry variety was discovered in Monterey County, Calif. in June 2008 and originated from a cross between the proprietary female parent '131N177' (unpatented) and the proprietary male parent '142N322' (unpatented). A single plant was selected for asexual propagation via tissue culture and vegetative cuttings in Shasta County, Calif. in 2008.

'DrisStrawFortyOne' underwent further testing in Monterey County, Calif. for six years (2008-2013). The present invention has been found to retain its distinctive characteristics through successive asexual propagations via stolons and tissue culture.

Plant Breeder's Rights for this variety have not been applied for. 'DrisStrawFortyOne' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Monterey County, Calif.

1. Dense plant;
2. Dark red fruit; and
3. Mid-season harvest maturity.

DESCRIPTION OF THE PHOTOGRAPHS

The accompanying color photographs show typical specimens of the new variety at various stages of development. The colors shown are as true as can be reasonably obtained by conventional photographic procedures. The photographs were taken from eight-month-old plants.

DESCRIPTION OF THE NEW VARIETY

Figure 1:
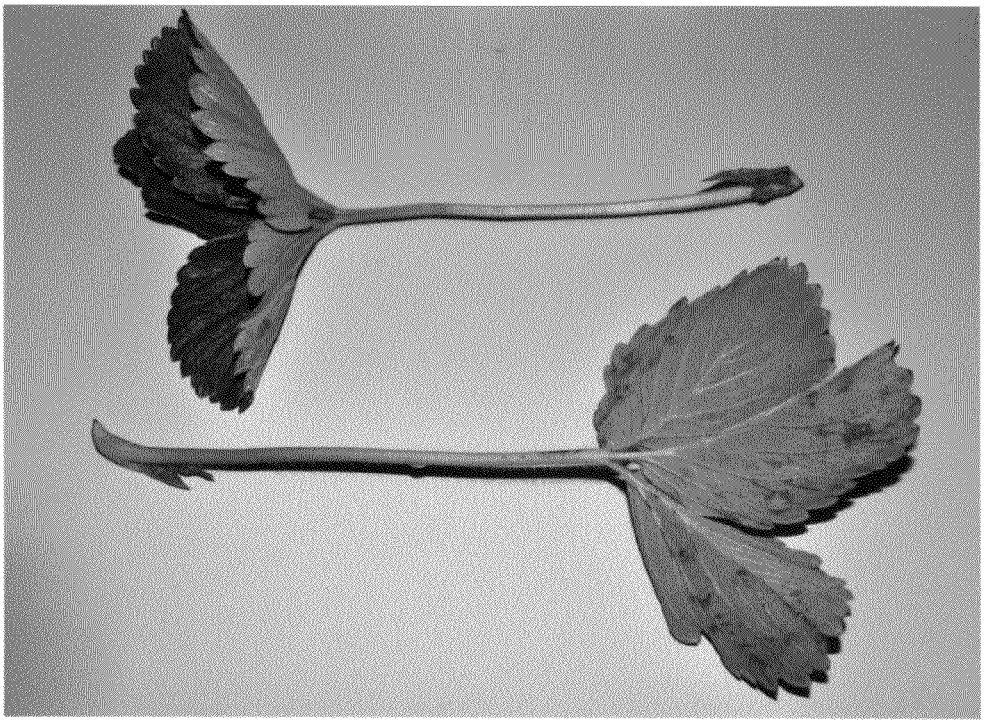
FIG. 1 shows upper and lower surfaces of the leaves of the plant with three leaflets.
Figure 2:
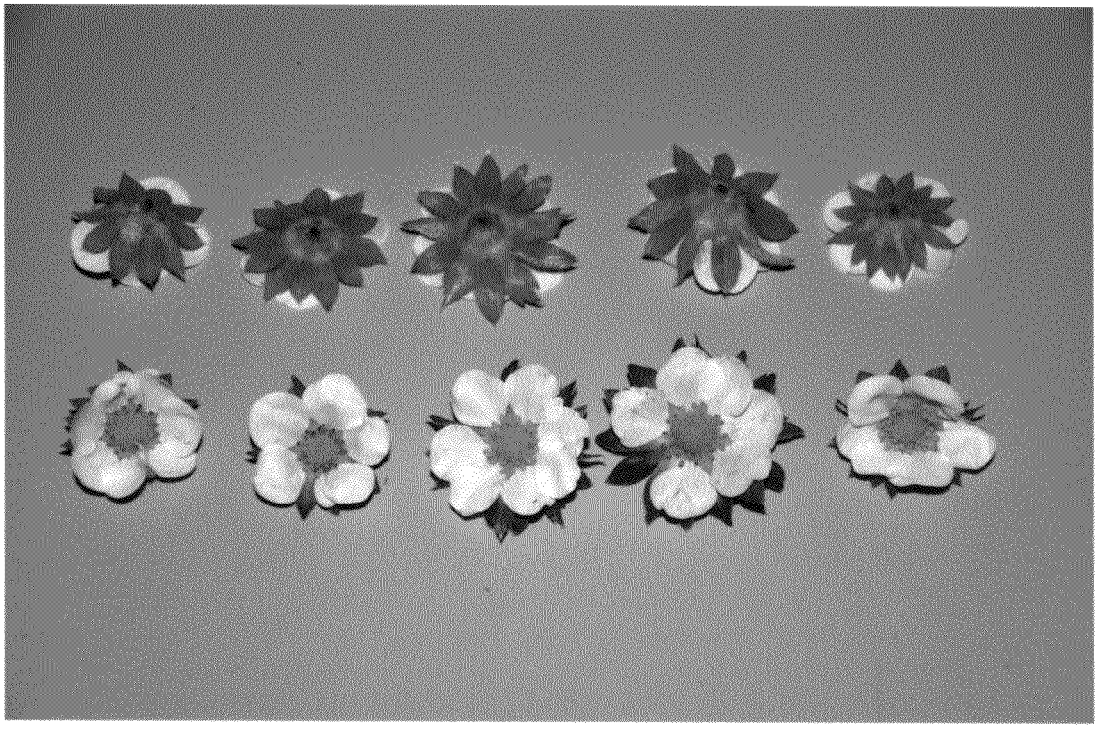
FIG. 2 shows both upper and lower surfaces of the flowers.
Figure 3:
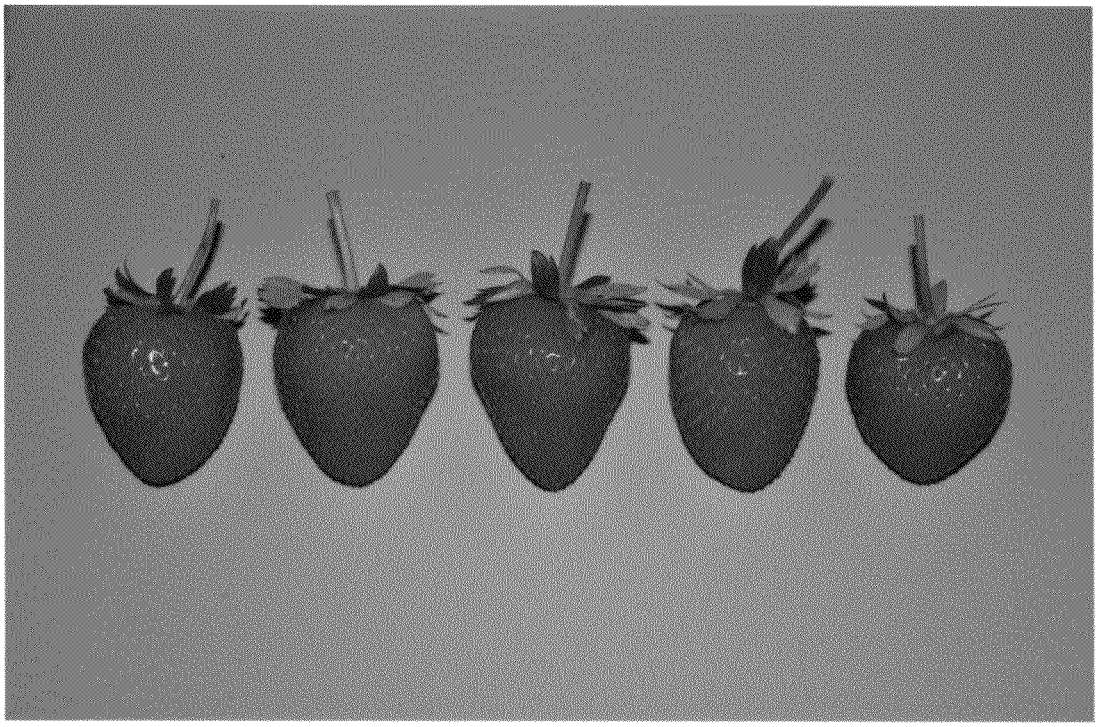
FIG. 3 shows the whole fruit.
Figure 4:
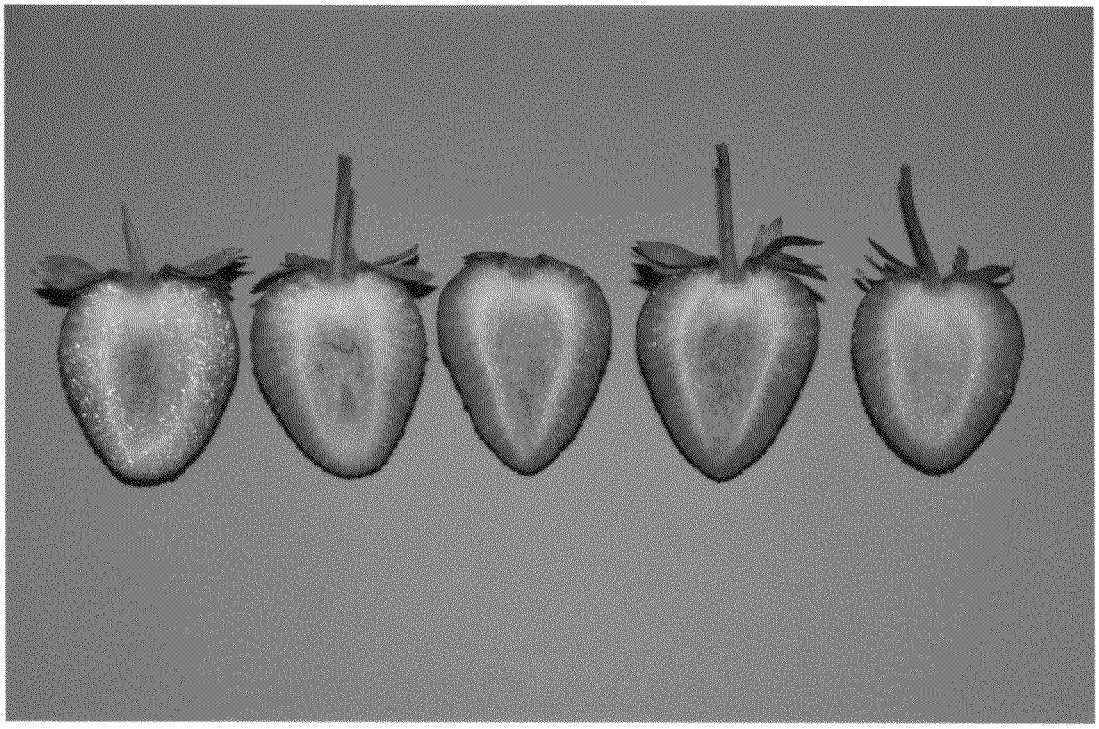
FIG. 4 shows the fruit in longitudinal cross-section.
Figure 5:
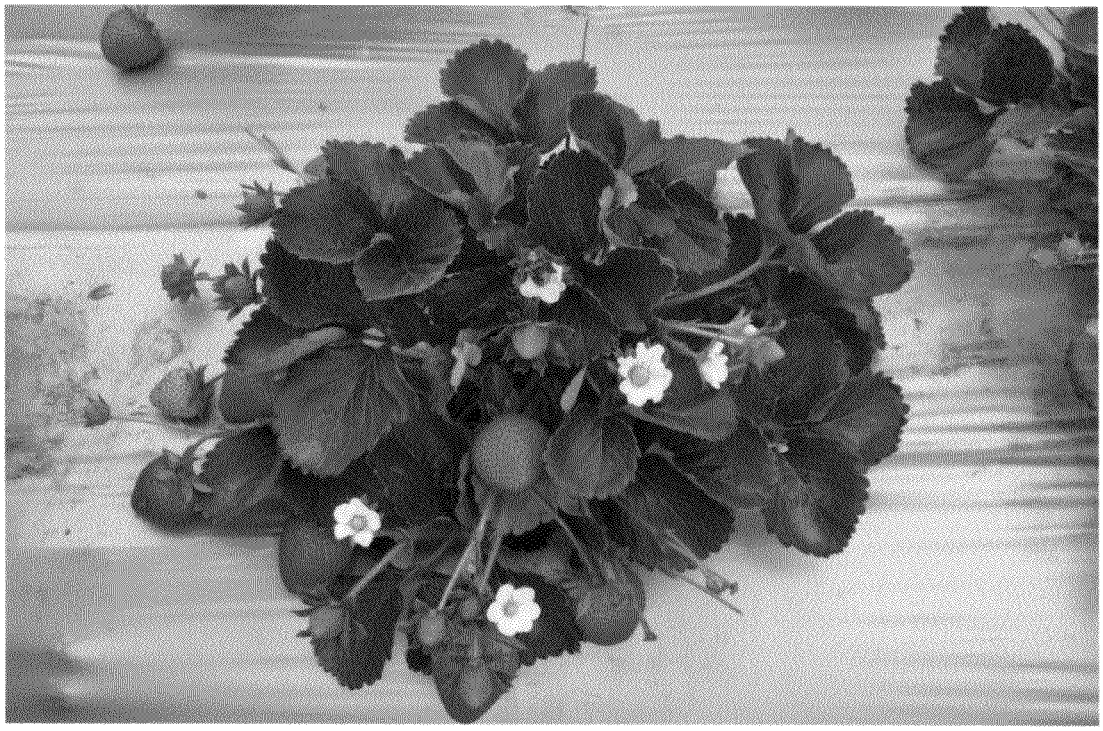
FIG. 5 shows the whole plant.

The following detailed descriptions set forth the distinctive characteristics of 'DrisStrawFortyOne'. The data which define these characteristics is based on observations taken in Monterey County, Calif. from 2008 to 2013. This description is in accordance with UPOV terminology. Color designations, color descriptions, and other phenotypical descriptions may deviate from the stated values and descriptions depending upon variation in environmental, seasonal, climatic, and cultural conditions. 'DrisStrawFortyOne' has not been observed under all possible environmental conditions. The botanical description of 'DrisStrawFortyOne' was taken from eight-month-old plants. Color references are primarily to The R.H.S. Colour Chart of The Royal Horticultural Society of London (R.H.S.) (2007 edition). Descriptive terminology follows the *Plant Identification Terminology, An Illustrated Glossary,* $2^{nd}$ edition by James G. Harris and Melinda Woolf Harris, unless where otherwise defined.

DETAILED BOTANICAL DESCRIPTION OF THE PLANT

Classification:

*Species.*—*Fragaria×ananassa.*
*Common name.*—Strawberry.
*Denomination.*—'DrisStrawFortyOne'.

Parentage:
*Female parent*.—The proprietary variety '131N177' (unpatented).
*Male parent*.—The proprietary variety '142N322' (unpatented).
Plant:
*Height*.—23.4 cm.
*Diameter*.—41.6 cm.
*Number of crowns/plant*.—3.
*Habit*.—Flat globose.
*Density of individual plant*.—Dense.
*Vigor* (*health and hardiness of plant*).—Medium.
Terminal leaflets:
*Size*.—Medium. Length: 7.0 cm. Width: 6.5 cm. Length/width ratio: 1.1 (Longer than broad).
*Number of teeth/terminal leaflet*.—24.
*Shape of teeth*.—Obtuse — serrate to crenate.
*Color*.—Upper surface: RHS 147A (Dark yellow-green). Lower surface: RHS 147B (Medium yellow-green).
*Shape in cross section*.—Concave.
*Blistering*.—Weak.
*Glossiness*.—Medium.
*Number of leaflets*.—Three only.
*Shape*.—Orbicular.
*Base shape*.—Rounded.
*Apex descriptor*.—Rounded.
*Variegation*.—Absent.
*Margin*.—Crenate.
*Margin profile*.—Revolute.
Petiole:
*Length*.—Short; 15.1 cm.
*Diameter*.—3.68 mm.
*Pubescence*.—Dense.
*Pose of hairs*.—Outwards — horizontal.
*Color*.—RHS 145A (Medium yellow-green).
*Bract frequency*.—1.
Petiolule:
*Length*.—10.70 mm.
*Diameter*.—1.74 mm.
*Color*.—RHS 145B (Medium yellow-green).
Stipule:
*Length*.—2.1 cm.
*Width*.—9.10 mm.
*Pubescence*.—Dense.
*Stipule anthocyanin coloration*.—Strong; RHS 68A (Medium red-purple).
Inflorescence:
*Position relative to foliage*.—Level.
*Number of flowers*.—Medium.
*Time of flowering* (*50% of plants at first flower*).—Medium.
*Flowering interval*.—Mid-February to late August.
*Flower size*.—Medium.
*Diameter*.—26.50 mm.
*Number of flowers per plant*.—47.1.
*Petals*.—Shape: Orbicular. Apex: Rounded. Base: Concavo-convex. Margin: Entire. Spacing: Touching. Length: 12.09 mm. Width: 11.51 mm. Length/width ratio: 1.1 (Longer than broad). Petal number per flower: 7. Color (upper surface): RHS NN155B (White).
*Calyx*.—Diameter: 27.82 mm. Diameter relative to corolla: Same size. Inner calyx diameter relative to outer: Same size. Insertion of calyx: In a basin — inserted. Pose of calyx segments: Reflexed — upwards. Size of calyx in relation to fruit: Slightly larger. Adherence of calyx: Medium.
*Sepal*.—Shape: Elliptical and ovate. Apex: Convex. Margin: Entire. Length: 11.56 mm. Width: 5.60 mm. Sepal number: 13.
*Receptacle color*.—RHS 151D (Light yellow-green).
*Stamen*.—Present. Anther color: RHS 163A (Medium greyed-orange).
*Pedicel*.—Attitude of hairs: Outwards — horizontal.
Fruiting truss:
*Length*.—Medium; 20.7 cm.
*Diameter at base of truss*.—2.85 mm.
*Number of berries per fruiting truss*.—4.
*Attitude at first picking*.—Semi-erect.
*Color at base of truss*.—RHS 144A (Medium yellow-green).
Fruit:
*Relative fruit size*.—Medium.
*Length*.—44.10 mm.
*Width*.—38.64 mm.
*Length/width ratio*.—1.1 (Longer than broad).
*Fruit hollow length*.—23.37 mm.
*Fruit hollow width*.—6.75 mm.
*Fruit hollow length/width ratio*.—3.5 (Much longer than broad).
*Fruit hollow center* (*cavity*).—Medium.
*Predominant fruit shape*.—Conical.
*Difference in shape between primary and secondary fruits*.—None or very slight.
*Evenness of fruit surface*.—Even or very slightly uneven.
*Fruit skin color*.—RHS 46A (Dark red).
*Evenness of fruit color*.—Even or very slightly uneven.
*Fruit glossiness*.—Medium.
*Achenes*.—Insertion of achenes: Above surface. Coloration (sunward side of berry): RHS 185A (Dark greyed-purple). Coloration (shaded side of berry): RHS 22A (Medium yellow-orange). Number per berry: 345. Weight (weight of achenes divided by total # seed): 0.01667 g. Width of band without achenes: Absent or very narrow.
*Firmness of flesh* (*when fully ripe*).—Firm.
*Color of flesh* (*excluding core*).—RHS 45C (Medium red) and RHS 36B (Light red).
*Color of core*.—RHS 37B (Medium red).
*Evenness of flesh color*.—Even.
*Distribution of flesh color*.—Marginal and central.
*Sweetness*.—Medium.
*Acidity*.—Weak.
*Texture when tasted*.—Medium.
*Type of bearing*.—Partially everbearing — partially remontant.
*Harvest interval*.—Mid-April to late October.
*Harvest maturity*.—Mid-season.
Disease and pest resistance:
*Tetranychus urticae*.—Moderately susceptible to susceptible.
*Botrytis fruit rot*.—Moderately resistant.
*Powdery mildew*.—Moderately susceptible.
*Verticillium wilt*.—Susceptible.
Reaction to stress:
*High temperatures*.—Moderately susceptible.
*Wind*.—Moderately susceptible.

COMPARISON WITH PARENTAL AND COMMERCIAL VARIETIES

When 'DrisStrawFortyOne' is compared to the female parent '131N177' (unpatented), 'DrisStrawFortyOne' has higher late yields, more erect plant habit, less leaf senescence and less fruit bronzing than '131N177'.

When 'DrisStrawFortyOne' is compared to the male parent '142N322' (unpatented), 'DrisStrawFortyOne' is a more compact plant and has larger fruit than '142N322'.

When 'DrisStrawFortyOne' is compared to the commercial variety 'DrisStrawNine' (U.S. Plant Pat. No. 20,733), 'DrisStrawFortyOne' has a dense plant with a flat globose habit and inflorescence positioned level with the foliage, whereas 'DrisStrawNine' has a medium dense plant with an upright habit and inflorescence positioned above the foliage. Additionally, 'DrisStrawFortyOne' has fruit with a medium adherence of the calyx, firm flesh and a medium hollow center, whereas 'DrisStrawNine' has fruit with a strong adherence of the calyx, medium firm flesh and a small hollow center.

When 'DrisStrawFortyOne' is compared to the commercial variety 'DrisStrawTwentyEight' (U.S. Plant Pat. No. 23,459), 'DrisStrawFortyOne' has medium sized terminal leaflets with obtuse to serrate to crenate shaped teeth and weak leaf blistering, whereas 'DrisStrawTwentyEight' has small terminal leaflets with rounded to crenate shaped teeth and medium leaf blistering. Additionally, 'DrisStrawFortyOne' has fruit with weak acidity and a medium hollow center, whereas 'DrisStrawTwentyEight' has fruit with strong acidity and a small hollow center.

We claim:

1. A new and distinct variety of strawberry plant named 'DrisStrawFortyOne' as described and shown herein.

* * * * *